United States Patent
Newman

(10) Patent No.: US 10,914,967 B2
(45) Date of Patent: Feb. 9, 2021

(54) SYSTEMS AND METHODS FOR PRINTING ON A CONTACT LENS

(71) Applicant: MENICON SINGAPORE PTE LTD., Singapore (SG)

(72) Inventor: Stephen D. Newman, Singapore (SG)

(73) Assignee: MENICON SINGAPORE PTE LTD., Singapore (SG)

( * ) Notice: Subject to any disclaimer, the term of this patent is extended or adjusted under 35 U.S.C. 154(b) by 0 days.

(21) Appl. No.: 14/890,086

(22) PCT Filed: May 8, 2014

(86) PCT No.: PCT/SG2014/000202
§ 371 (c)(1),
(2) Date: Nov. 9, 2015

(87) PCT Pub. No.: WO2014/182248
PCT Pub. Date: Nov. 13, 2014

(65) Prior Publication Data
US 2016/0116764 A1    Apr. 28, 2016

(30) Foreign Application Priority Data

May 8, 2013   (SG) .................................. 201303566

(51) Int. Cl.
| | | |
|---|---|---|
| *G02C 7/04* | (2006.01) | |
| *A61K 9/00* | (2006.01) | |
| *B29C 41/22* | (2006.01) | |
| *B29C 41/04* | (2006.01) | |
| *A61K 47/34* | (2017.01) | |
| *B29D 11/00* | (2006.01) | |
| *B29L 11/00* | (2006.01) | |
| *B29K 83/00* | (2006.01) | |
| *B29K 105/00* | (2006.01) | |

(52) U.S. Cl.
CPC ............ *G02C 7/049* (2013.01); *A61K 9/0051* (2013.01); *A61K 47/34* (2013.01); *B29C 41/045* (2013.01); *B29C 41/22* (2013.01); *B29D 11/00038* (2013.01); *B29D 11/00096* (2013.01); *B29D 11/00115* (2013.01); *B29D 11/00865* (2013.01); *B29D 11/00894* (2013.01); *G02C 7/046* (2013.01); *B29K 2083/00* (2013.01); *B29K 2105/0061* (2013.01); *B29K 2105/0094* (2013.01); *B29L 2011/0041* (2013.01)

(58) Field of Classification Search
None
See application file for complete search history.

(56) References Cited

U.S. PATENT DOCUMENTS

| | | | | |
|---|---|---|---|---|
| 4,099,859 A | * | 7/1978 | Merrill | B29D 11/00 351/159.33 |
| 7,799,249 B2 | * | 9/2010 | Goodenough | G02B 1/043 264/1.38 |
| 2004/0130676 A1 | * | 7/2004 | Doshi | B29D 11/00317 351/159.25 |
| 2005/0270474 A1 | | 12/2005 | Odhner | |
| 2008/0143003 A1 | | 6/2008 | Phelan | |
| 2013/0018360 A1 | | 1/2013 | Dockendorf et al. | |
| 2013/0093994 A1 | | 4/2013 | Ando et al. | |

FOREIGN PATENT DOCUMENTS

| | | |
|---|---|---|
| CN | 102985871 A | 3/2013 |
| CN | 103052364 A | 4/2013 |
| JP | S5278453 A | 7/1977 |
| JP | H04270312 A | 9/1992 |
| JP | 2005531810 A | 10/2005 |
| JP | 2007538113 A | 12/2007 |
| JP | 2009008848 A | 1/2009 |
| JP | 2011076105 A | 4/2011 |
| JP | 3179308 U | 10/2012 |
| JP | 2013067741 A | 4/2013 |
| JP | 2013524275 A | 6/2013 |
| JP | 5369273 B1 | 12/2013 |
| JP | 2013250352 A | 12/2013 |
| JP | 2016519339 A | 6/2016 |
| TW | 201313255 A | 4/2013 |
| WO | 2004003636 A1 | 1/2004 |
| WO | 2005036236 A2 | 4/2005 |
| WO | 2005102675 A2 | 11/2005 |
| WO | 2011123180 A1 | 10/2011 |

(Continued)

OTHER PUBLICATIONS

PCT International Search Report for PCT International Patent Application No. PCT/SG2014/000202, dated Jul. 29, 2014.
Supplementary European Search Report for corresponding European Patent Application No. EP14794798, dated Sep. 26, 2016.
English translation of Chinese Search Report from corresponding Chinese Patent Application No. 201480039314.0, dated Mar. 20, 2017.
Search Report for corresponding Taiwan Patent Application No. 103116252, dated May 17, 2017.
First Examination Report for European Patent Application No. 14794798.0, dated Apr. 12, 2018 (5 pages).

(Continued)

*Primary Examiner* — Tigabu Kassa
(74) *Attorney, Agent, or Firm* — Dorsey & Whitney LLP

(57) ABSTRACT

One embodiment of a contact lens includes a lens body configured to fit directly on the surface of the eye and legible characters positioned on the lens body. Another embodiment of a contact lens comprises a lens body including polymeric material and a lens enhancing material (e.g., ink, silicone material, medicament material, and the like) encapsulated in the polymeric material. The lens enhancing material can be in the form of isolated sections distributed in the surrounding polymeric material. Methods of making contact lenses include forming a first lens layer including a first surface, forming a pattern on the first surface, and forming a second lens layer over the pattern.

14 Claims, 8 Drawing Sheets

(56) References Cited

FOREIGN PATENT DOCUMENTS

| | | |
|---|---|---|
| WO | 2011161920 A1 | 12/2011 |
| WO | 2012016098 A1 | 2/2012 |
| WO | 2014182248 A1 | 11/2014 |

OTHER PUBLICATIONS

Search Report issued for Taiwan Patent Application No. 103116252, dated Mar. 13, 2018, English translation (1 page).
Second Office Action for Chinese Patent Application No. 201480039314.0, dated Dec. 5, 2017 (13 pages).

* cited by examiner

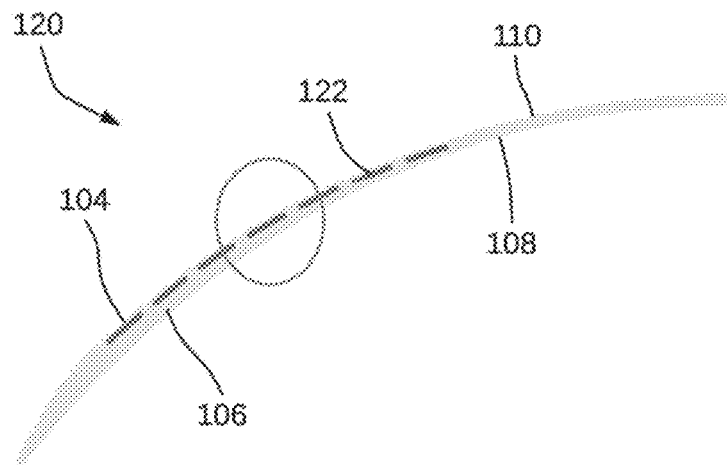
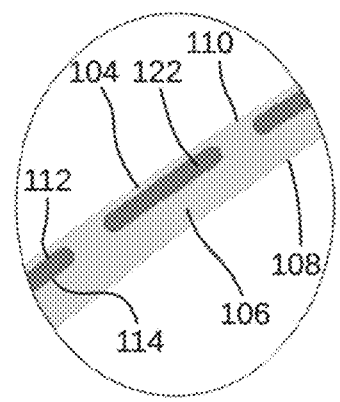
Fig. 13
Fig. 14
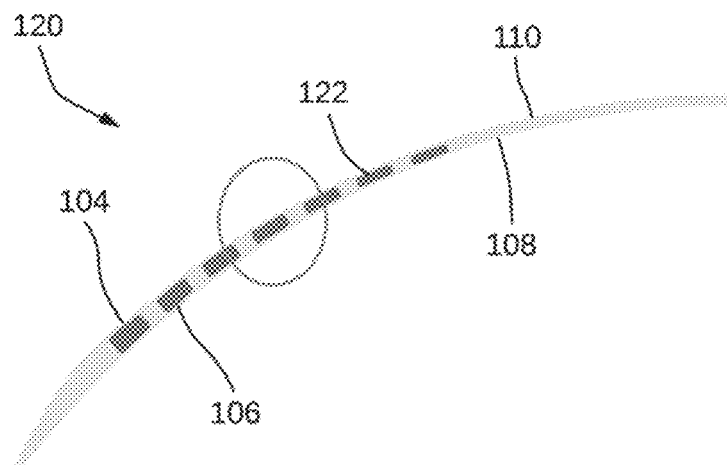
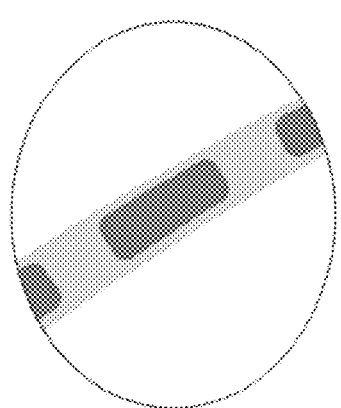
Fig. 15
Fig. 16

SYSTEMS AND METHODS FOR PRINTING ON A CONTACT LENS

BACKGROUND

Contact lenses have improved substantially in the last twenty years. They are now made of materials that offer better wetting properties and higher oxygen permeability. They can also be used to change the appearance of the user's eyes. For example, color contacts can be used to change the appearance of the user's iris.

Even with these improvements, contact lenses still suffer from a number of drawbacks. For example, it would be beneficial to provide a contact lens that is increasingly durable, wettable, and/or oxygen permeable. It would also be beneficial to provide a contact lens that includes legible characters on the lens.

SUMMARY

A number of representative embodiments are provided to illustrate the various features, characteristics, and advantages of the disclosed subject matter. It should be understood that the features, characteristics, advantages, etc., described in connection with one embodiment can be used separately or in various combinations and sub-combinations with other features described in connection with other embodiments.

A contact lens includes a lens enhancing material that alters one or more properties of the contact lens. The lens enhancing material can alter properties such as the appearance of the lens, which in turn alters the appearance of the eye. For example, the lens enhancing material can include an ink pattern that enhances the appearance of the iris, limbal ring, pupil, or other portion of the eye.

The lens enhancing material can also enhance properties of the contact lens such as wettability and oxygen permeability. For example, the lens enhancing material can include silicone material arranged in combination with hydrogel material to provide increased wettability and oxygen permeability.

The lens enhancing material can also be used to deliver medicaments such as drugs, vitamins, and the like. For example, the lens enhancing material can include an antibiotic material that is slowly released into the eye to eliminate infections. The lens enhancing material can be positioned in a peripheral zone and/or an optic zone of the contact lens.

In one embodiment, a contact lens includes a lens body configured to fit directly on the surface of the eye. The lens body includes a plurality of legible characters visible to a third party observer when the contact lens is on the eye. The plurality of legible characters are formed by ink included as part of the lens body. The legible characters can include writing characters that form one or more words such as "I Love You" or "Imagine Me." They can also include letters, numbers, glyphs, and geometric shapes. The legible characters can be positioned on and/or encapsulated in the lens body.

The characters can be positioned in any suitable location but are preferably printed on the peripheral zone of the contact lens to prevent them from affecting the user's vision. The characters can be black and white or preferably color. In one embodiment, the lens body includes a first lens layer and a second lens layer with the legible characters positioned between the two layers.

In another embodiment, the lens enhancing material forms markings on the contact lens that have the appearance of and/or enhance the appearance of an iris, limbal ring, pupil (make it appear dilated more than normal), or other portion of the eye. The ink can include thickeners to enhancers its ability to adhere to the polymeric material.

In another embodiment, the contact lens comprises a lens body including a polymeric material and the lens enhancing material encapsulated, encased, or enclosed in the polymeric material. The lens enhancing material can include any of the materials mentioned above including ink, silicone material (e.g., silicone polymers, silicone hydrogel material, and the like), medicament material (e.g., drug delivery material and vitamin delivery material), and the like.

In another embodiment, the contact lens comprises a lens body including a polymeric material and isolated sections of lens enhancing material encapsulated in the surrounding polymeric material. The lens enhancing material is isolated in physically separate sections to enhance the structural integrity of the contact lens. The lens enhancing material can be any of those materials mentioned above.

In one embodiment, the lens body comprises a polymeric material including a pattern of isolated sections of silicone material encapsulated in the surrounding polymeric material. The silicone material can include silicone hydrogel material or silicone polymers. In one embodiment, the silicone material is at least substantially entirely silicone polymers (little or no hydrogel polymers) to enhance the oxygen permeability of the contact lens.

The contact lens can be made using any suitable process. In one embodiment, a method for making the contact lens includes: (1) forming a first lens layer including a first surface, (2) forming a pattern on the first surface of the first lens layer and/or depositing a lens enhancing material on the first surface of the first lens layer, and (3) forming a second lens layer over the pattern or lens enhancing material.

The layers can be formed using contact lens manufacturing processes such as spin casting, cast moulding, and/or rotational moulding. Preferably, the first lens layers is formed by pouring liquid polymeric material into a mould, spinning and partially curing the polymeric material. The second lens layer can be formed in a similar fashion except that it is fully cured. The pattern can be formed and/or the lens enhancing material deposited using a printing process such as a tamp printing process or liquid jet (e.g., inkjet) printing process.

The Summary is provided to introduce a selection of concepts in a simplified form that are further described below in the Detailed Description. The Summary and the Background are not intended to identify key concepts or essential aspects of the disclosed subject matter, nor should they be used to constrict or limit the scope of the claims. For example, the scope of the claims should not be limited based on whether the recited subject matter includes any or all aspects noted in the Summary and/or addresses any of the issues noted in the Background.

DRAWINGS

The preferred and other embodiments are disclosed in association with the accompanying drawings. Throughout the drawings, identical reference numbers designate similar, but not necessarily identical, elements. As illustrated below:

FIG. 13 is a cross sectional view of one embodiment of a contact lens having a pattern of lens enhancing material in the peripheral zone.

FIG. 14 is a blown up view of a section of the contact lens shown in FIG. 13.

FIG. 15 is a cross sectional view of another embodiment of a contact lens having a pattern of lens enhancing material in the peripheral zone.

FIG. 16 is a blown up view of a section of the contact lens shown in FIG. 15.

DETAILED DESCRIPTION

Contact lenses including a variety of lens enhancing materials are disclosed. The lens enhancing material alters one or more properties of the contact lens in a desired manner. Examples of ways that the lens enhancing material can alter the contact lens include: altering the appearance of the contact lens, which in turn alters the appearance of the eye, altering the wettability of the contact lens, altering the oxygen permeability of the contact lens, and the like.

Figure 1:
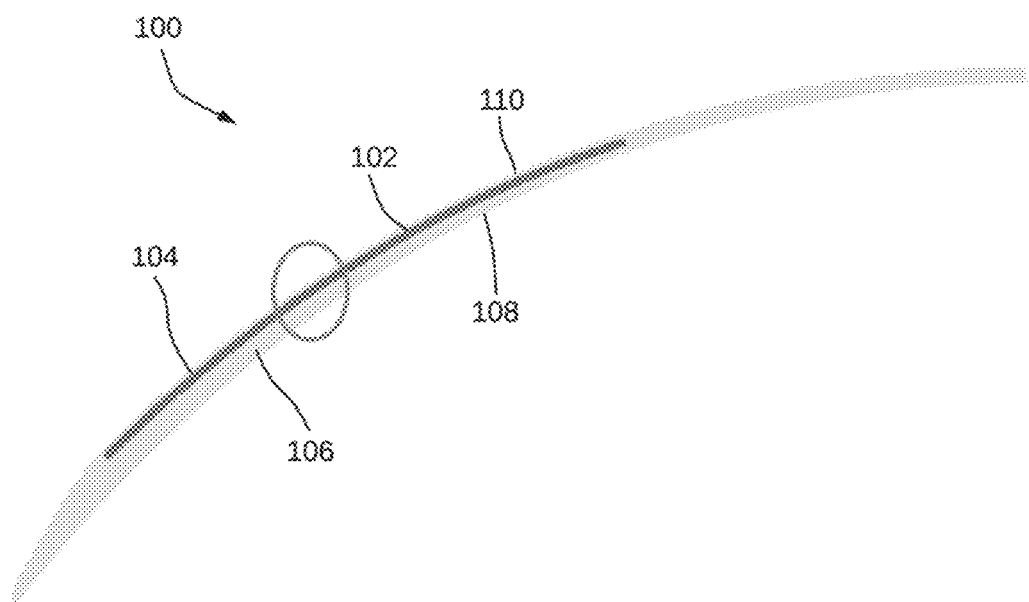
FIG. 1 is cross sectional view of one embodiment of a contact lens having visible markings in the peripheral zone.

FIG. 1 shows one embodiment of a contact lens 100 having visible markings 102 that form one or more patterns on the contact lens 100. The contact lens 100 includes a first lens layer 104 and a second lens layer 106 with the markings 102 positioned between the layers 104, 106. It should be appreciated that although the markings 102 are shown positioned between the layers 104, 106, the markings 102 could also be positioned on the outer, convex surface of the contact lens 100.

The combination of the layers 104, 106, and the markings 102 forms the lens body of the contact lens 100. The layers 104, 106 can be formed of the same material or of different materials. In one embodiment, the layers 104, 106 are formed of the same material so that there is no discernible boundary layer in the contact lens 100 either from a visual standpoint or from a physical properties standpoint. The layers 104, 106 can be coupled together using any suitable method. In one embodiment, the layers 104, 106 are covalently bonded to each other to give the contact lens 100 greater internal structural strength. For example, the layers 104, 106 can be polymerized together.

In another embodiment, the layers 104, 106 are formed of different materials. The layers 104, 106 can still have no discernible boundary layer from either a visual standpoint or a physical properties standpoint. The different materials can provide different properties to the layers 104, 106 making it possible to customize the properties of each side of the contact lens 100.

It should be appreciated that regardless whether the layers 104, 106 are made of the same or different materials, it is also possible to form a discernible boundary layer between the layers 104, 106. Preferably, the boundary layer should not interfere with the visual clarity of the contact lens 100.

The first lens layer 104 and the second lens layer 106 can be made from any material suitable for use in contact lenses. For example, the layers 104, 106 can be made of any silicone material and/or hydrogel material. The layers 104, 106 can be formed of any number of appropriate polymers including, but in no way limited to: Low Water (<50% water) Nonionic Hydrogel Polymers: tefilcon, tetrafilcon A, crofilcon, helfilcon A&B, mafilcon, polymacon, and hioxifilcon B. Low Water Nonionic Silicone Hydrogel Polymers: lotrafilcon A, lotrafilcon B, galyfilcon A, senofilcon A, sifilcon A, comfilcon A, and enfilcon A. High Water (>50% water) Nonionic Hydrogel Polymers: lidofilcon B, surfilcon A, lidofilcon A, alfafilcon A, omafilcon A, vasurfilcon A, hioxifilcon A, hioxifilcon D, nelfilcon A, hilafilcon A, and acofilcon A. Low Water Ionic Hydrogel Polymers: bufilcon A, deltafilcon A, and phemfilcon A. Low Water Ionic Silicone Hydrogel Polymers: balafilcon A. High Water Ionic Hydrogel Polymers: bufilcon A, perfilcon, etafilcon A, focofilcon A, ocufilcon B, ocufilcon C, ocufilcon D ocufilcon E, ocufilcon F, phemfilcon A, methafilcon A, methafilcon B, and vilfilcon A.

These materials include various combinations of monomers, polymers, and other materials to form the final polymer. For example, common components of these materials include HEMA, HEMA-GMA, and the like.

In one embodiment, the layers 104, 106 are made at least substantially entirely of hydrogel polymers without any silicone. This may be desirable to increase the wettability of the contact lens 100. In another embodiment, the layers 104, 106 are made of silicone hydrogel material.

In one embodiment, the layers 104, 106 are configured so that the inner surface 108 and the outer surface 110 of the contact lens 100 is made mostly or entirely of hydrogel polymers. In this configuration, the hydrophilic hydrogel polymers contact the surface of the eye and the back of the eyelid instead of the hydrophobic silicone polymers. The layers 104, 106 can still include silicone polymers, but the silicone polymers are not present at the surfaces 108, 110 of the contact lens 100.

The first lens layer 104 and the second lens layer 106 can be shaped and sized based on a variety of factors, including the shape and size of the users eye and various optical properties to be achieved by the contact lens. In some embodiments, the lens layers 104, 106 each have a thickness of approximately 0.01 mm to approximately 0.09 mm. The total thickness of the contact lens 100 can be approximately 0.1 mm to approximately 0.14 mm. The thickness of the lens layers 104, 106 can vary at different locations on the contact lens 100. For example, the second lens layer 106 can be thicker near the outer edge of the contact lens 100 than in the optic zone as shown in FIG. 1.

The layers 104, 106 can have different thicknesses with one layer 104, 106 being thicker or thinner than the other layer 104, 106. For example, the first lens layer 104 in FIG. 1 is substantially thinner than the second lens layer 106. This makes it so the markings 102 are positioned closer to the outer surface 110 of the contact lens 100. It should be appreciated that either layer 104, 106 can have any desired thickness or thickness profile.

The first lens layer 104 includes a first surface 112 (alternatively referred to as a first lens surface) positioned opposite a second surface, which is the outer surface 110 of the contact lens 100. The first surface 112 can have a concave shape and generally serve as the surface of the first lens layer 104 upon which the markings 102 are formed.

The second lens layer 106 includes a first surface 114 positioned opposite a second lens surface, which is the inner surface 108 of the contact lens 100. The first surface 114 can have a convex shape that corresponds to the first surface 112 of the first lens layer 104 so that when the two layers 112, 114 are brought together the markings 102 on the first surface 112 are encapsulated. The layers 112, 114 should be formed in a manner that eliminates any gaps or void spaces within the contact lens 100.

It should be appreciated that the contact lens 100 can include additional layers. For example, one lens enhancing material can be positioned between the layers 104, 106 and another lens enhancing material can be positioned between lens 106 and a third lens layer (not shown). The first lens enhancing material can be the markings 102 and the second lens enhancing material can be a medicament material.

The markings 102 are configured to be visible to a third party observer when the contact lens 100 is in the user's eye. The markings 102 can alter and/or enhance the appearance of the user's eyes. The markings 102 can be used to alter or enhance the appearance of the user's iris, limbal ring, pupil, and the like. For example, the markings 102 can be used to change the color of the user's eyes.

FIGS. 3-8 show various embodiments of markings 102 that are configured to have the appearance of and/or enhance the appearance of an iris. The markings 102 can be black and white but are preferably in color. For example, the markings 102 in FIG. 5 can have different shades of green so that a user wearing the contact lens 100 has green colored eyes. Likewise, the markings 102 in FIG. 6 can be different shades of bright red to change the user's eye color to red.

Figure 7:
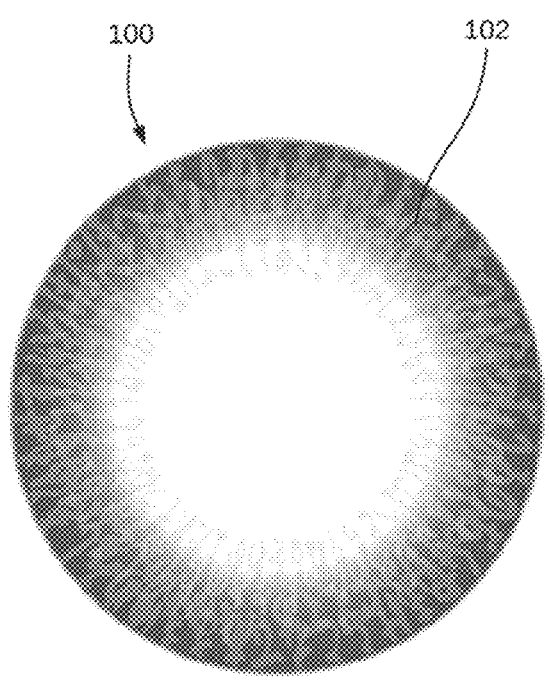
FIGS. 7-8 show front views of various embodiments of marking patterns that can be included in the peripheral zone of the contact lens shown in FIG. 1. These figures are designed to enhance the appearance of the iris with markings that resemble Asian writing characters.
Figure 8:
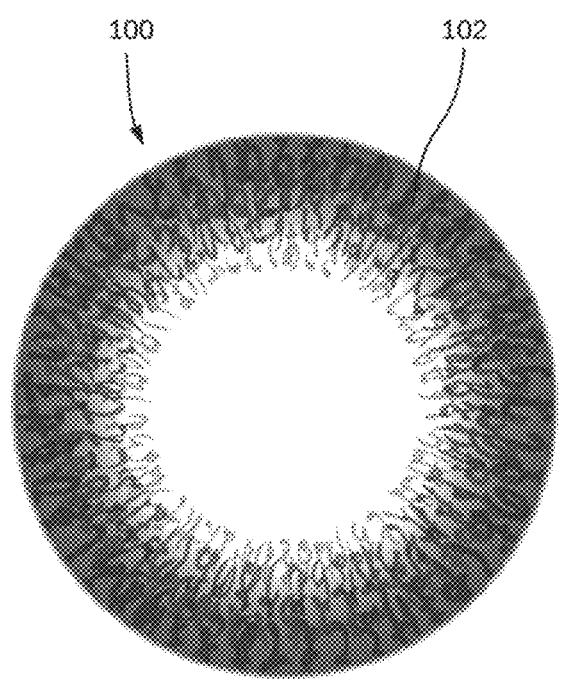
Figure 9:
FIGS. 9-12 show front views of different embodiments of marking patterns that can be included in the peripheral zone of the contact lens shown in FIG. 1. These figures include legible characters positioned over a dark background.
Figure 10:
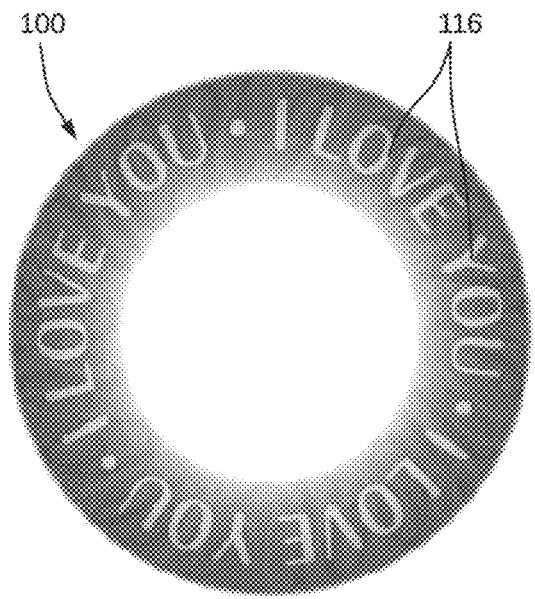
Figure 11:
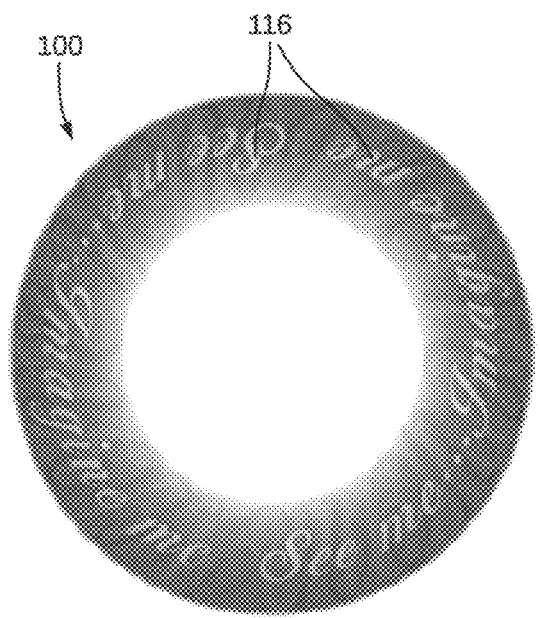
Figure 12:
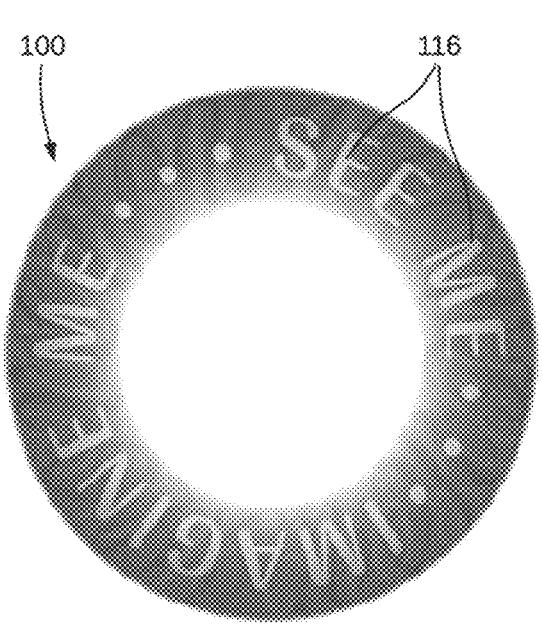
Figure 17:
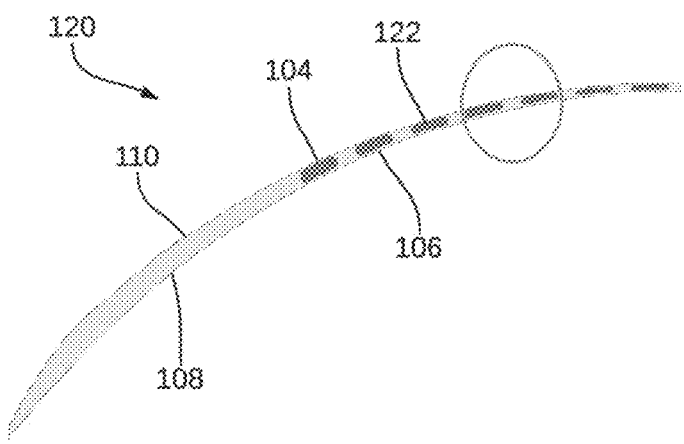
FIG. 17 is a cross sectional view of one embodiment of a contact lens having a pattern of lens enhancing material in the optic zone.
Figure 18:
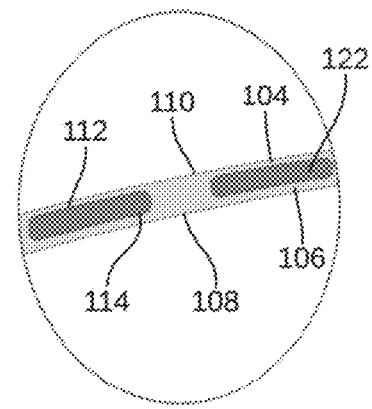
FIG. 18 is a blown up view of a section of the contact lens shown in FIG. 17.
Figure 19:
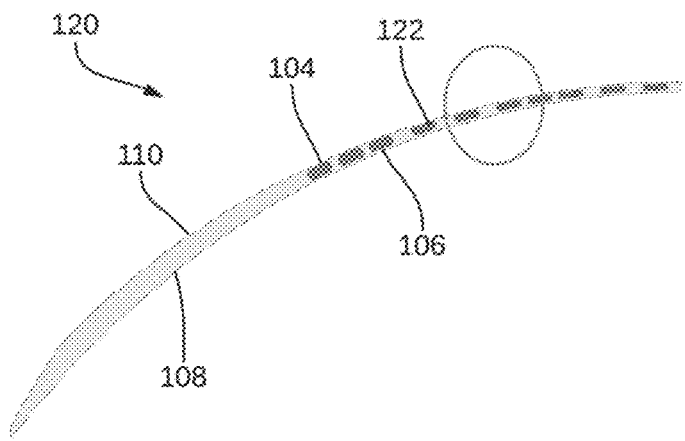
FIG. 19 is a cross sectional view of another embodiment of a contact lens having a pattern of lens enhancing material in the optic zone.
Figure 20:
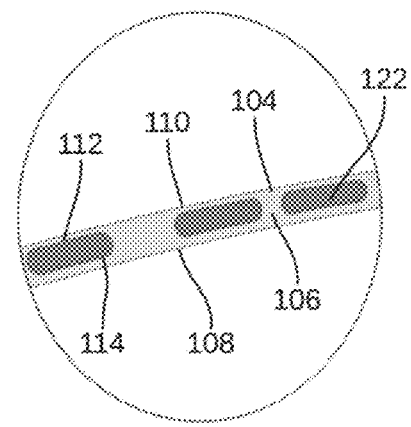
FIG. 20 is a blown up view of a section of the contact lens shown in FIG. 19.
Figure 21:
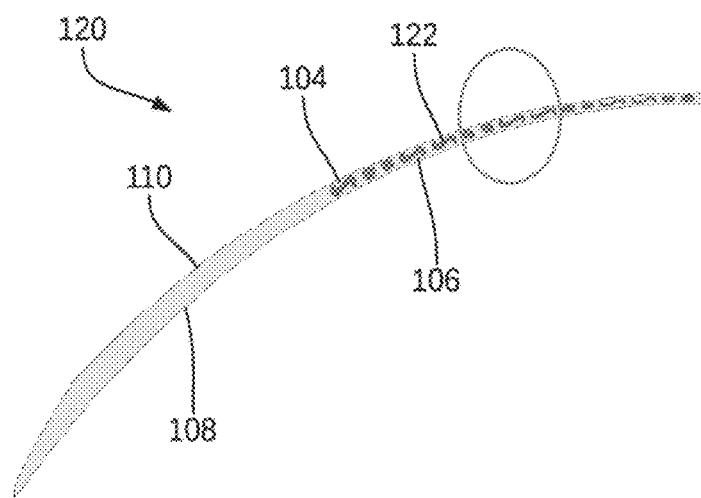
FIG. 21 is a cross sectional view of another embodiment of a contact lens having a pattern of lens enhancing material in the optic zone.
Figure 22:
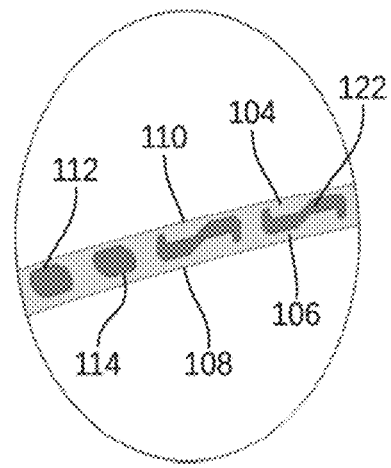
FIG. 22 is a blown up view of a section of the contact lens shown in FIG. 21.

FIGS. 7-8 show one embodiment of the contact lens 100 configured to enhance the appearance of the iris with markings 102 that resemble Asian writing characters positioned over a solid background. The writing characters extend past the area where the solid background ends toward the optic zone of the contact lens 100.

It should be noted that in some embodiments the markings 102 are generally limited to the peripheral zone of the contact lens 100 to avoid interfering with the user's vision. For example, the markings 102 can be arranged circumferentially around the peripheral zone of the contact lens 100. This is the preferable configuration when the lens enhancing material is visible to a third party observer. However, in other situations where the lens enhancing material is clear, then it can be positioned in the peripheral zone, optic zone, or both.

In one embodiment, the markings 102 form a plurality of legible characters 116 on the contact lens 100. The legible characters 116 can include letters, numbers, glyphs, and geometric shapes. The size, style, and orientation of the characters is virtually unlimited. The color of the characters is also unlimited and in some embodiments, the legible characters 116 can include a plurality of colors.

In one embodiment, the legible characters 116 are legible writing characters in English, Japanese, Chinese, Korean, or any other language. The legible characters 116 can be configured to form at least one or more words. For example, the legible characters 116 can form an at least two word saying such as "I Love You," "See me," or "Imagine Me."

The legible characters 116 are visible to a third party observer when the contact lens 100 is in the user's eye. The characters 116 can be visible and legible to a third party observer having normal visual acuity (20/20) at a distance of approximately 7 cm to approximately 120 cm. The characters 116 can be visible and legible to a third party observer having normal visual acuity at a distance of approximately 7 cm, approximately 15 cm, approximately 23 cm, approximately 30 cm, approximately 45 cm, approximately two feet, approximately 60 cm, or approximately 120 cm.

Figure 24:
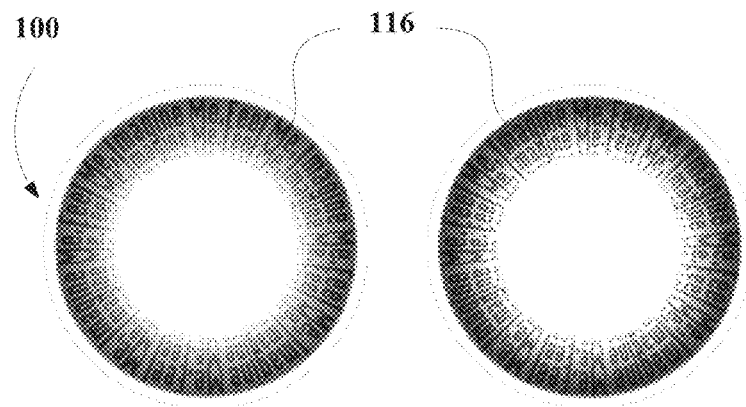
FIGS. 24-26 show front views of different embodiments of marking patterns that can be included in the peripheral zone of the contact lens shown in FIG. 1. These figures include legible characters positioned over a dark background.
Figure 25:
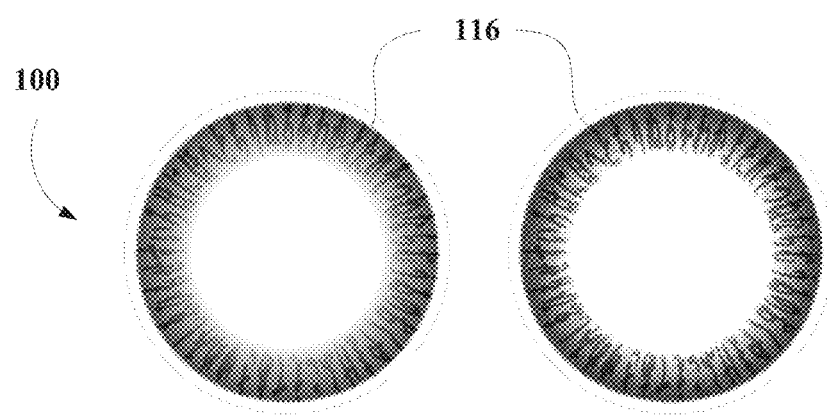
Figure 26:
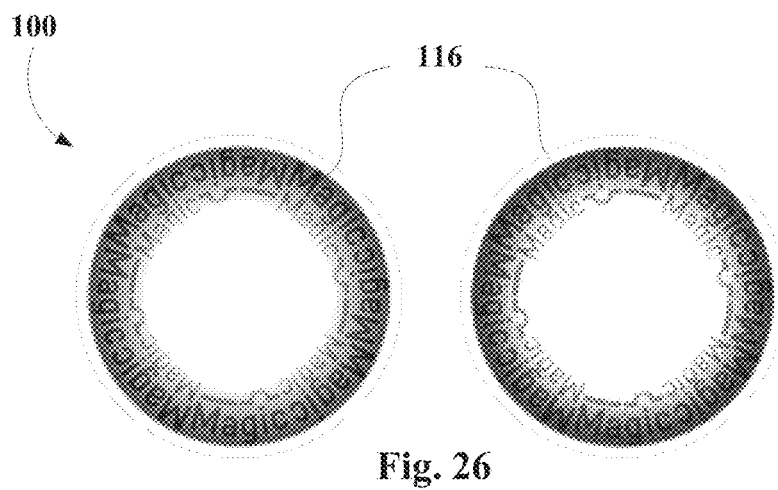

FIGS. 9-12 show various embodiments of the contact lens 100 having legible characters 116. The legible characters 116 form the words "I Love You" in FIGS. 9-10 and the words "See me . . . Imagine me" in FIGS. 11-12. The legible characters 116 are arranged circumferentially in the peripheral zone of the contact lens 100. The characters 116 are positioned over a color background that matches the color of the characters. Similarly, FIGS. 24-26 illustrate various embodiments of the contact lens 100 having legible characters 116. The legible characters 116 form the words "Feel Me Imagine Me" in FIG. 24, the characters for "i ro ha" and the words and pattern for "magic," including a texture gradient arranged circumferentially in the peripheral zone of the contact lens 100. The characters 116 are positioned over a color background that matches the color of the characters.

The markings 102 can be made using any suitable technique. In one embodiment, the markings 102 are made with ink deposited on the first surface 112 of the first lens layer 104. It should be appreciated that although the markings 102 are shown as a continuous layer in FIGS. 1-2, the actual cross-sectional configuration of the markings 102 depends on the desired design.

It should be appreciated that the markings 102 can be formed by any ink that is suitable for use with contact lenses. Suitable inks include, but are not limited to those available from Unicorn (Taiwan) Chemical Co. Ltd. Additional inks can be found in U.S. Pat. No. 6,731,408 ("Bensky et al."), U.S. Pat. No. 5,713,963 ("Bensky"), and U.S. Pat. No. 7,354,959 ("Tucker et al."), which inks are incorporated herein by reference. In some embodiments, the ink is a type that incorporates into the material of the first lens layer 104 and/or the second lens layer 106.

A thickener can be added to the ink in order to modify the viscosity and prevent the ink from running after it is formed on the first lens layer 104. Any thickener safe for use in contact lenses and which will improve the viscosity of the ink can be used. In one embodiment, the thickener can be polyethylene glycol and/or glycerol.

The ink can have any suitable viscosity that allows the ink to remain in place after being deposited on the first surface 112 of the first lens layer 104. In one embodiment, wherein the pad or tamp printing method is used, the ink has a viscosity of approximately 1.0 Pa·s to approximately 1.8 Pa·s and preferably a viscosity of approximately 1.4 Pa·s. According to yet another exemplary embodiment, if ink-jet or other printing methodologies are used, the ink may have a viscosity less than 1.0 Pa·s.

The thickness of the markings 102 formed on the first lens layer 104 can vary anywhere from approximately 2 microns to approximately 120 microns. According to one embodiment, the thickness of the markings 102 formed on the first lens layer 104 can vary anywhere from approximately 5 microns to approximately 20 microns. The thickness of the markings 102 can be uniform throughout the contact lens 100 or can be variable.

FIG. 13 shows another embodiment of a contact lens 120 where the lens enhancing material includes silicone material 122, which forms a pattern on the contact lens 120. The presence of silicone material means that the contact lens 120 can be considered a silicone hydrogel contact lens. The silicone material 122 increases the oxygen permeability of the contact lens 100 making it more comfortable for the user to wear for longer periods of time.

Figure 2:
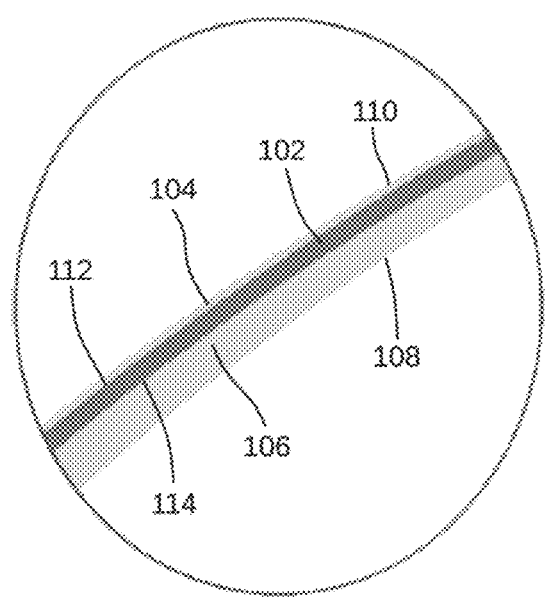
FIG. 2 is a blown up view of a section of the contact lens shown in FIG. 1.
Figure 3:
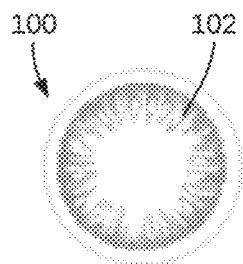
FIGS. 3-6 show front views of various embodiments of marking patterns that can be included in the peripheral zone of the contact lens shown in FIG. 1. These figures are designed to have the appearance of the iris and/or enhance the appearance of the iris.
Figure 4:
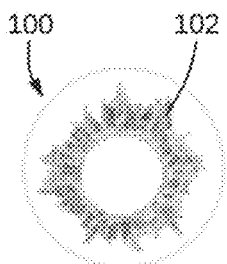
Figure 5:
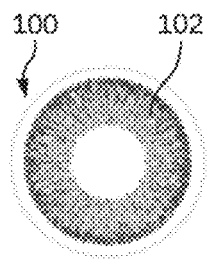
Figure 6:
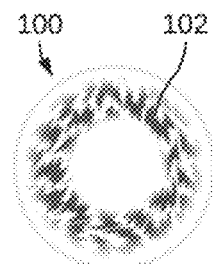

The contact lens 120 includes many of the components shown in connection with the contact lens 100 in FIGS. 1-2. The same reference numerals are used to designate similar components. It should be appreciated that similarly designated components in FIGS. 13-22 need not be the same as those in FIGS. 1-2, although they can be.

The combination of the layers 104, 106 and the silicone material 122 forms the lens body of the contact lens 120. The silicone material 122 can be any suitable material. In one embodiment, the silicone material 122 is at least substantially entirely made up of silicone polymers without any hydrogel polymers. This configuration maximizes the oxygen permeability of the contact lens 120. It should be appreciated that the silicone material 122 can also include a combination of silicone polymers and hydrogel polymers in varying amounts.

The layers 104, 106 can be made of any of the materials mentioned above. It should be noted, however, that it is preferable for the outer surface 110 and inner surface 108 to be made principally of hydrogel polymers to increase the wettability of the contact lens 120 and particularly the portion of the contact lens 120 that contacts the eye and/or eyelid.

The silicone material 122 is arranged in a pattern of isolated sections encapsulated in the surrounding polymeric material of layers 104, 106. The isolated sections allow the layers 104, 106 to meet and be coupled together between the sections. This configuration imparts greater structural strength to the contact lens 120. It should be noted that the gaps between the sections are filled in by the second lens layer 106 when it is coupled to the first lens layer 104.

In one embodiment, the isolated sections of silicone material 122 are not covalently bonded to the surrounding polymeric material that forms layers 104, 106. In other embodiments, the isolated sections can be covalently bonded to the surrounding polymeric material. If the silicone material 122 is covalently bonded to the layers 104, 106, then the silicone material could also be provided as a distinct layer.

FIGS. 15-22 show additional embodiments of the contact lens 120. One thing these figures illustrate is that the sections can be any suitable size and arranged in any suitable manner. In one embodiment, the silicone material 122 is arranged as a uniform grid where the sections are all approximately the same size. In another embodiment, the silicone material 122 is arranged in randomly sized and positioned sections throughout the contact lens 120.

The thickness of the silicone material 122 can also vary widely. For example, the silicone material in FIGS. 13-14 is relatively thin compared to the thickness of the contact lens 120. However, the thickness of the silicone material 122 in FIGS. 15-16 is relatively thick compared to the thickness of the contact lens 120.

It is generally preferable to make the silicone material 122 as thick as possible to increase oxygen permeability and eye health. The corollary to this is that it is preferable to minimize the thickness of the polymeric material between the silicone material 122 and the outer surface 110 and the inner surface 108. In one embodiment, the polymeric material between the silicone material 122 and each of the surfaces 108, 110 is no more than 0.001 mm thick, no more than 0.002 mm thick, no more than 0.005 mm thick, no more than 0.01 mm thick, no more than 0.02 mm thick, no more than 0.03 mm thick, or no more than 0.04 mm thick.

It should be appreciated that the silicone material 122 can be positioned in the peripheral zone and/or the optic zone of the contact lens 120. FIGS. 13-16 show embodiments where the silicone material 122 is posited in the peripheral zone of the contact lens 120, and FIGS. 17-22 show embodiments where the silicone material 122 is positioned in the optic zone of the contact lens 120. It should be appreciated that the silicone material 122 can also be positioned in both the peripheral zone and the optic zone of the contact lens 120.

It should be appreciated that additional embodiments of a contact lens can be created using different lens enhancing materials such as medicaments and the like. The medicaments can be deposited on the first lens layer 104 in the same manner as the markings 102 and/or the silicone material 122. The medicament and/or the polymeric material surrounding the medicament can be configured to provide the desired release rate to provide a therapeutic effect to the user's eye.

Figure 23:
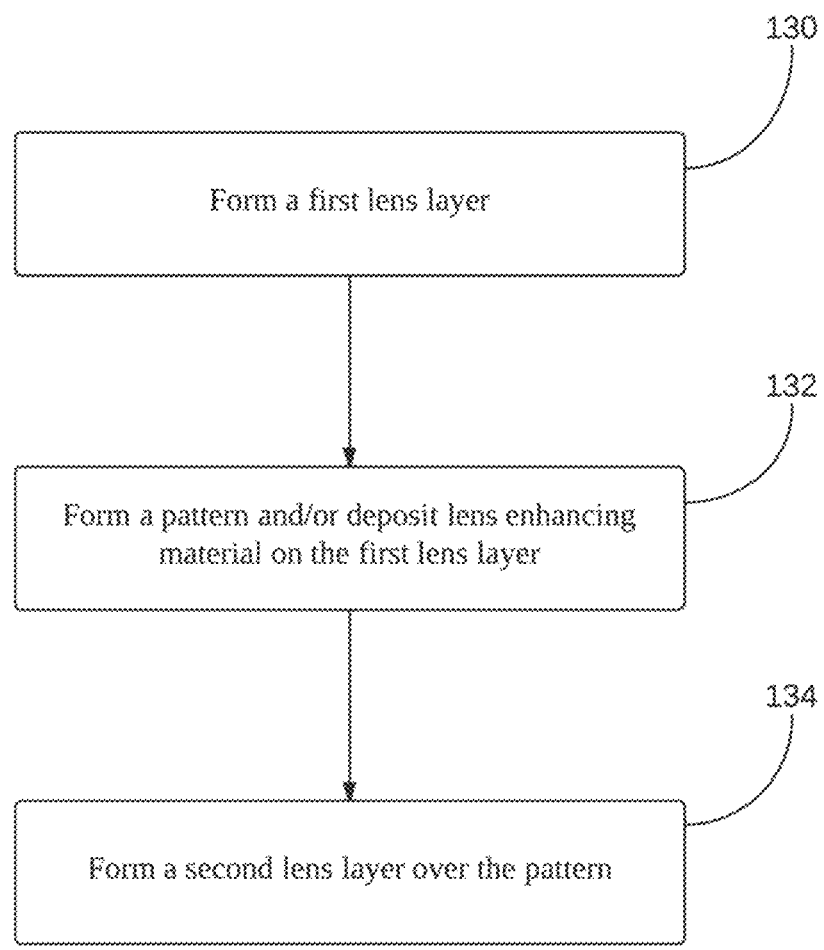
FIG. 23 is a flowchart of one embodiment of a method for making the contact lens shown in FIGS. 1-22.

Methods of manufacturing contact lenses having patterns of legible characters formed thereon are also described as follows. The broad outline of the method is shown in FIG. 23. The method begins by forming the first lens layer having a first lens surface at step 130. A pattern of lens enhancing material is formed and/or the lens enhancing material is deposited on the first surface at step 132. The second lens layer is formed over the lens enhancing material on the first surface at step 134.

It should be appreciated that the result of this method is to encapsulate or enclose the lens enhancing material between the first and second lens layers. This serves to protect the lens enhancing material and impart desirable properties to the lens enhancing material—e.g., the lens enhancing material includes silicone material that increase oxygen permeability.

The first lens layer can be formed at step 130 using any suitable process. Examples of suitable processes include spin casting, cast moulding, and/or turning. In one embodiment, the first lens layer is formed using a mould and spinning and curing techniques. A portion of liquid polymeric material is poured into the mould, spun, and cured to form the first lens layer. The spinning and curing steps can be partial so that the first lens layer is not fully cured at the completion of step 130.

The mould used to form the first lens layer can be any mould suitable for use in the formation of contact lenses. In one embodiment, the mould is laser etched to impart the desired optical properties to the final contact lens. The mould can be designed and shaped in any of variety of ways to achieve the desired optical properties for the final contact lens product.

The amount of liquid polymeric material poured into the mould is generally not limited and can be adjusted based on the desired final properties of the contact lens, including physical properties such as thickness and various optical properties.

The polymeric material can be any of the materials described above in connection with layers 104, 106. In one embodiment, the polymeric material used to form the first lens layer is at least substantially entirely hydrogel polymers such as HEMA-GMA. In another embodiment, the polymeric material can include a silicone hydrogel material.

The spinning and curing steps can varied based on the desired properties of the final contact lens. For example, it is generally desirable to cure the first lens layer sufficiently to allow it to support the lens enhancing material but not so much that it cannot adequately bond to the second lens layer when it is added. This may be achieved by partially curing the lens material to the gel point, at which stage cross-links have been formed within the partially cured monomer, In one embodiment, the first lens layer is formed of a non-homogenous lamination of other materials. The different materials can form separate and distinct domains in the first lens layer. In one embodiment, the non-homogenous lamination is three dimensional in nature meaning that the domains are non-homogenous in all three directions.

The pattern is formed on the first surface of the first lens layer at step 132. The manner in which the pattern is formed on the first lens layer is generally not limited and can include any printing methods that are suitable for use in printing on contact lenses. Exemplary printing techniques include, but are not limited to, pad printing, plate printing, etch printing, dot matrix printing, dye sublimation and carrier sheet (laser printing), and photosensitive elements that receive subsequent laser treatment.

In one embodiment, the printing method is a tamp printing technique. Tamp printing techniques is one method of pad printing that uses a laser etched pad to transfer the lens enhancing material to the first surface of the first lens layer. The pad tamps a reservoir of lens enhancing material (e.g., ink) each time before it tamps the lens enhancing material on the first surface. Machines capable of printing in this fashion are available from TAMPOPRINT in Germany.

In another embodiment, the lens enhancing material can be printed on the first lens layer using an liquid jet printing system. In one embodiment, the liquid is ink and the printing system is an ink jet printing system. However, in another embodiment, the liquid can include the silicone material.

The second lens layer is formed over the pattern at step 134. The second lens layer is formed in such a manner that the pattern and/or lens enhancing material is sandwiched between or encapsulated by the first lens layer and the second lens layer.

In one embodiment, step 134 is performed in a similar or identical manner to the step 130 of forming the first lens layer, including pouring liquid polymeric material into the mould and spinning and curing it to form the second lens layer. Other techniques known to those of ordinary skill in the art can also be used for forming the second lens layer.

It should be noted that the liquid polymeric material will fill any gaps between the lens enhancing material. In effect, this means that the second lens layer includes the polymeric material positioned between the lens enhancing material.

In one embodiment, the same mould is used for forming the first lens layer and the second lens layer. Alternatively, a separate mould can be used. The mould can be any mould suitable for use in the formation of a contact lens.

The amount of polymeric material poured into the mould is generally not limited and can be adjusted based on the desired final properties of the contact lens, including physical properties such as thickness and various optical properties. In many situations, the second lens layer requires additional polymeric material to fill any gaps between the lens enhancing material and/or to provide a thicker layer than the first lens layer (FIG. 1).

The material used to form the second lens layer can be the same or different than that used to form the first lens layer. Any of the materials described above can be used to form the second lens layer. In one embodiment, the second lens layer is at least substantially entirely made of hydrogel polymers. In another embodiment, the second lens layer includes a silicone hydrogel material.

In some embodiments of the contact lens and manufacturing methods described herein, the blur at the edge of the contact lens (myopia) can be controlled by virtue of the lens enhancing material. The lens enhancing material can be applied in a manner that uses defractive optics and/or build the asphere of the periphery in order to achieve this result.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure the term shall mean," etc.).

References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope.

The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be given their broadest interpretation in view of the prior art and the meaning of the claim terms.

As used herein, spatial or directional terms, such as "left," "right," "front," "back," and the like, relate to the subject matter as it is shown in the drawings. However, it is to be understood that the described subject matter may assume various alternative orientations and, accordingly, such terms are not to be considered as limiting.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

All ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed is:

1. A contact lens comprising:
a lens body configured to fit directly on the surface of an eye;
wherein the lens body includes a first lens layer and a second lens layer formed at least substantially entirely of hydrogel material; and
a lens enhancing silicone material positioned between the first lens layer and the second lens layer; and
wherein the lens enhancing silicone material includes a plurality of isolated sections of silicone encapsulated in and physically separate from the surrounding hydrogel material;
wherein the lens enhancing silicone material increases wettability and oxygen permeability of the contact lens; and
wherein each isolated section of the plurality of isolated sections separates the first lens layer and the second lens layer at the respective isolated section.

2. The contact lens of claim 1, wherein the lens body comprises a low water nonionic hydrogel material.

3. The contact lens of claim 1, wherein the lens enhancing silicone material is at least substantially made up of silicone polymers and substantially without hydrogel polymers.

4. The contact lens of claim 1, wherein the lens enhancing silicone material is encapsulated in isolated sections between the first lens layer and the second lens layer.

5. The contact lens of claim 1, wherein the lens body includes an inner surface defined by the first lens layer and an outer surface defined by the second lens layer, and
a thickness of the lens body between each of the inner surface or the outer surface of the lens body and the lens enhancing silicone material is no more than about 0.010 mm.

6. The contact lens of claim 1, wherein the lens enhancing silicone material is arranged circumferentially on the lens body.

7. The contact lens of claim 1, wherein the lens enhancing silicone material is positioned in a peripheral zone of the lens body.

8. The contact lens of claim 1, wherein the hydrogel material comprises low water nonionic hydrogel material.

9. The contact lens of claim 1, wherein the lens enhancing silicone material further comprises at least one of drug delivery and vitamin delivery to an eye.

10. The contact lens of claim 1, wherein the lens enhancing silicone material further comprises an ink or a medicament material.

11. The contact lens of claim 1, comprising:
wherein the lens body includes a polymeric material.

12. The contact lens of claim 11, wherein the isolated sections of lens enhancing silicone material are not covalently bonded to the surrounding polymeric material.

13. The contact lens of claim 11, wherein the lens body includes an inner surface and an outer surface, wherein the inner surface or the outer surface is made at least substantially entirely of a hydrogel polymers.

14. The contact lens of claim 13, wherein the polymeric material at the inner surface or the outer surface of the of the lens body is at least substantially entirely hydrogel polymers to a thickness of at least approximately 0.005 mm, at least approximately 0.010 mm, at least approximately 0.015 mm, or at least approximately 0.02 mm.

* * * * *